United States Patent
Takahashi

(10) Patent No.: US 10,828,245 B2
(45) Date of Patent: Nov. 10, 2020

(54) COMPOSITION FOR WHITENING TEETH

(71) Applicant: GC CORPORATION, Sunto (JP)

(72) Inventor: Makoto Takahashi, Tokyo (JP)

(73) Assignee: GC CORPORATION, Sunto (JP)

( * ) Notice: Subject to any disclaimer, the term of this patent is extended or adjusted under 35 U.S.C. 154(b) by 0 days.

(21) Appl. No.: 16/489,593

(22) PCT Filed: Oct. 24, 2017

(86) PCT No.: PCT/JP2017/038317
§ 371 (c)(1),
(2) Date: Aug. 28, 2019

(87) PCT Pub. No.: WO2018/168045
PCT Pub. Date: Sep. 20, 2018

(65) Prior Publication Data
US 2019/0388319 A1 Dec. 26, 2019

(30) Foreign Application Priority Data
Mar. 16, 2017 (JP) .................. 2017-050878

(51) Int. Cl.
A61K 8/42 (2006.01)
A61K 8/22 (2006.01)
A61K 8/37 (2006.01)
A61K 8/49 (2006.01)
A61Q 11/00 (2006.01)

(52) U.S. Cl.
CPC ................. A61K 8/42 (2013.01); A61K 8/22 (2013.01); A61K 8/37 (2013.01); A61K 8/4973 (2013.01); A61Q 11/00 (2013.01)

(58) Field of Classification Search
CPC .......... A23L 2/52; A23L 33/10; A23L 27/204; A23L 27/2054; A23L 27/00; A23L 27/20; A23L 27/2052; A23L 27/2056; A23L 27/30; A23L 27/36; A23L 27/80; A23L 27/86; A23L 27/88; A23L 2/385; A23L 2/56; A23L 2/60; A61K 47/22; A61K 8/4933; A61K 31/381; A61K 31/415; A61K 9/0014; A61K 2300/00; A61K 36/67; A61K 3/81; A61K 31/425; A61K 31/515; A61K 45/06; A61K 8/22; A61K 8/37; A61K 8/42; A61K 8/4973
See application file for complete search history.

(56) References Cited

U.S. PATENT DOCUMENTS

2005/0031552 A1 2/2005 Mori et al.
2009/0249557 A1* 10/2009 Maki ................ C11D 1/72
8/137

FOREIGN PATENT DOCUMENTS

JP 2005-060267 A 3/2005

* cited by examiner

*Primary Examiner* — Nannette Holloman
(74) *Attorney, Agent, or Firm* — Sughrue Mion, PLLC

(57) ABSTRACT

An object is to provide a composition for whitening teeth superior in a flavor without deteriorating the whitening performance, the composition for whitening teeth including: at least one of urea peroxide, and hydrogen peroxide; isoamyl propionate; ethyl n-octanoate; ethyl 3-methyl-3-phenylglycidate; and a compound having a β-dicarbonyl structure in an amount of 0 mass % to 0.001 mass % on the basis of the composition.

1 Claim, No Drawings

COMPOSITION FOR WHITENING TEETH

CROSS REFERENCE TO RELATED APPLICATIONS

This application is a National Stage of International Application No. PCT/JP2017/038317, filed Oct. 24, 2017, claiming priority to Japanese Patent Application No. 2017-050878, filed Mar. 16, 2017.

TECHNICAL FIELD

The present invention relates to a composition for whitening teeth which is used for whitening stained teeth.

BACKGROUND ART

Generally, whiteness of teeth is considered to be an important factor for beauty. Teeth are strongly desired to be whitened, and cases of requesting tooth whitening are increasing. This tooth whitening is basically to make stains on teeth colorless or to remove stains from teeth, by a chemical reaction.

The mainstream of a composition for whitening teeth as described above is to use peroxides such as hydrogen peroxide and urea peroxide as an active ingredient for whitening (for example, Patent Literature 1). These peroxides generate hydroxyl radicals and decompose coloring matter, to have a whitening function.

It is known that flavor is incorporated into such a composition for whitening teeth to make the flavor of the composition good flavor for the purpose of easing patient's unpleasant feeling, etc. Patent Literature 1 also describes that flavor may be incorporated as necessary.

CITATION LIST

Patent Literature

Patent Literature 1: JP 2005-060267 A

SUMMARY OF INVENTION

Technical Problem

A conventional composition for whitening teeth has a problem of retarding effect of peroxides that are an active ingredient for whitening when flavor is incorporated, to deteriorate whitening performance.

In view of the problem, an object of the present invention is to provide a composition for whitening teeth superior in a flavor without deteriorating the whitening performance.

Solution to Problem

As a result of an intensive study of the inventor of the present invention, the inventor found that a composition for whitening teeth having a good flavor can be obtained without deteriorating the whitening performance by containing a specific flavor ingredient, and either none of or if so just a little amount of a compound having a predetermined structure, to complete the present invention.

One aspect of the present invention is a composition for whitening teeth, the composition comprising: at least one of urea peroxide, and hydrogen peroxide; isoamyl propionate; ethyl n-octanoate; ethyl 3-methyl-3-phenylglycidate; and a compound having a β-dicarbonyl structure in an amount of 0 mass % to 0.001 mass % on the basis of the composition.

Advantageous Effects of Invention

According to the present invention, a composition for whitening teeth can have a good flavor as keeping the whitening performance.

DESCRIPTION OF EMBODIMENTS

A composition for whitening teeth according to the present invention contains at least one of urea peroxide and hydrogen peroxide as an active ingredient for whitening teeth, isoamyl propionate, ethyl n-octanoate, and ethyl 3-methyl-3-phenylglycidate as a flavor ingredient, and either no more than 0.001 mass % or none of a compound having a β-dicarbonyl structure.

This makes it possible for the composition for whitening teeth to have a good flavor without deteriorating but as keeping a high whitening performance.

Only one of urea peroxide and hydrogen peroxide may be employed, or they may be employed in combination. The amount of urea peroxide and/or hydrogen peroxide is preferably 1 mass % to 40 mass % on the basis of the total composition for whitening teeth. The amount of no less than 1 mass % makes the effect of whitening teeth difficult to deteriorate. The amount of no more than 40 mass % can make the whitening performance of the composition for whitening teeth not too high.

The composition for whitening teeth may contain a polyalcohol as the base. Examples of the polyalcohol include polyglycerins such as glycerol and diglycerin, propylene glycol, dipropylene glycol, sorbitol, mannitol, ethylene glycol, diethylene glycol, polyethylene glycol, and monomethyl ether. Two or more of them may be employed in combination.

The amount of the polyalcohol is preferably 15 mass % to 85 mass % on the basis of the total composition for whitening teeth. The amount of no less than 15 mass % improves adhesin to teeth, to improve the effect of whitening teeth. The amount of no more than 85 mass % makes the composition for whitening teeth not drip down and excellent in usability.

Water may be contained as the base of the composition for whitening teeth instead of or together with the polyalcohol. When water is contained, the amount thereof is preferably 1 mass % to 80 mass % on the basis of the total composition for whitening teeth. The amount of no less than 1 mass % improves adhesin to teeth, to improve the effect of whitening teeth. The amount of no more than 80 mass % makes the storage stability of the composition for whitening teeth difficult to deteriorate.

The composition for whitening teeth may contain a thickener to improve the viscosity of the base. This makes it possible to surely adhere urea peroxide and/or hydrogen peroxide, which is an active ingredient, to teeth. When the polyalcohol is contained as the base, a thickener swellable in the polyalcohol is preferably used.

A thickener swellable in the polyalcohol makes it possible to improve the viscosity of the composition for whitening teeth, to make the composition easy to adhere to surfaces of teeth. Any material that makes it possible to improve the viscosity of the composition for whitening teeth may be employed as such a thickener swellable in the polyalcohol without any specific limitation. Examples thereof include sodium Carboxymethyl cellulose, sodium alginate, carboxy polymethylene, carboxymethyl cellulose, carboxymethyl cellulose sodium salt, carboxy polymethylene, calcium carboxymethylcellulose, methyl vinyl ether-maleic anhydride copolymers, sodium starch glycolate, sodium starch phosphate, sodium polyacrylate, methyl cellulose, microcrystalline cellulose, hydroxypropyl cellulose, polyvinylpyrrolidone, and vinyl polymers. Two or more of them may be employed in combination.

When a thickener swellable in the polyalcohol is contained in the composition for whitening teeth, the amount thereof is preferably 0.1 mass % to 15 mass % on the basis of the total composition for whitening teeth although the thickener is used as suitably adjusted according to the material to be used. The amount of no less than 0.1 mass % can make the composition for whitening teeth easy to stay on surfaces of teeth. The amount of no more than 15 mass % makes the composition for whitening teeth not have too high a viscosity and excellent in usability.

The composition for whitening teeth may contain an inorganic thickener instead of or together with the thickener swellable in the polyalcohol. Any thickener that has been conventionally used for a composition for whitening teeth may be employed as the inorganic thickener. Examples thereof include calcium carbonate, calcium silicate, magnesium silicate, silica powder, various glasses, amorphous hydrous silicic acid, fumed silica, and titanium dioxide. Two or more of them may be employed in combination.

When the inorganic thickener is contained in the composition for whitening teeth, the preferred amount thereof is the same as that of the thickener swellable in the polyalcohol.

In the present invention, isoamyl propionate, ethyl n-octanoate, and ethyl 3-methyl-3-phenylglycidate are contained as a specific flavor ingredient, and either no more than 0.001 mass % or none of a compound having a β-dicarbonyl structure is contained. This makes it possible for the composition for whitening teeth to have a good flavor without retarding the function of the active ingredient for whitening teeth but as keeping the whitening performance.

When a compound having a β-dicarbonyl structure is contained, the amount thereof is more preferably no more than 0.0001 mass %.

Isoamyl propionate, which is also referred to as propioric acid isoamyl ester, is represented by the following formula (1):

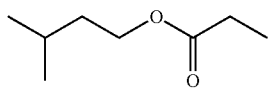

(1)

Isoamyl propionate is one of aromatic ingredients of fruits such as bananas, grapes and apples.

The amount of isoamyl propionate is preferably 0.001 mass % to 2 mass % on the basis of the total composition for whitening teeth. The amount of no less than 0.001 mass % makes the composition for whitening teeth have a good flavor that is easy to be sensed. The amount of no more than 2 mass % does not make the flavor of the composition for whitening teeth too strong. The amount of isoamyl propionate is more preferably 0.01 mass % to 0.5 mass % on the basis of the total composition for whitening teeth.

Ethyl n-octanoate, which is also referred to as ethyl octanoate, is represented by the following formula (2):

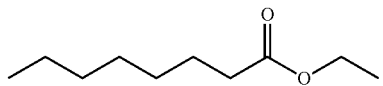

(2)

Ethyl n-octanoate is one of aromatic ingredients of fruits such as apricots and pineapples.

The amount of ethyl n-octanoate is preferably 0.001 mass % to 2 mass % on the basis of the total composition for whitening teeth. The amount of no less than 0.001 mass % makes the composition for whitening teeth have a good flavor that is easy to be sensed. The amount of no more than 2 mass % does not make the flavor of the composition for whitening teeth too strong. The amount of ethyl n-octanoate is more preferably 0.01 mass % to 0.5 mass % on the basis of the total composition for whitening teeth.

Ethyl 3-methyl-3-phenylglycidate, which is also referred to as ethyl methyl phenylglycidic acid ethyl ester or ethyl methyl phenylglycidate, is represented by the following formula (3):

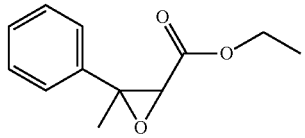

(3)

Ethyl 3-methyl-3-phenylglycidate is one of aromatic ingredients of strawberries.

The amount of ethyl 3-methyl-3-phenylglycidate is preferably 0.001 mass % to 2 mass % on the basis of the total composition for whitening teeth. The amount of no less than 0.001 mass % makes the composition for whitening teeth have a good flavor that is easy to be sensed. The amount of no more than 2 mass % does not make the flavor of the composition for whitening teeth too strong. The amount of ethyl 3-methyl-3-phenylglycidate is more preferably 0.01 mass % to 0.5 mass % on the basis of the total composition for whitening teeth.

The ratio of the amount of ethyl n-octanoate to that of isoamyl propionate is preferably 0.2 to 0.8. This range makes the composition for whitening teeth have a further good flavor that is easy to be sensed.

The ratio of the amount of ethyl 3-methyl-3-phenylglycidate to that of isoamyl propionate is preferably 0.7 to 1.3. This range makes the composition for whitening teeth have a further good flavor that is easy to be sensed.

"β-dicarbonyl structure" in the compound having a β-dicarbonyl structure is represented by the following formula (4):

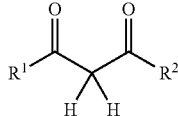

(4)

Here, $R^1$ and $R^2$ are any.

Examples of the compound having a β-dicarbonyl structure include acetoacetic acid ethyl ester (ethyl acetoacetate)

represented by the formula (5), methyl acetoacetate represented by the formula (6), and diethyl malonate represented by the formula (7).

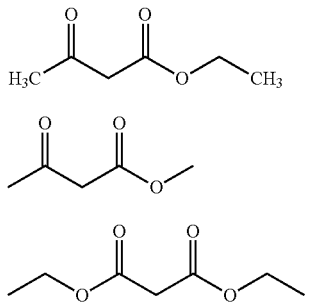

The composition for whitening teeth of the present invention contains either no more than 0.001 mass % or none of such a compound having a β-dicarbonyl structure. That is, the amount of the compound having a 31-dicarbonyl structure in the composition for whitening teeth is 0 mass % to 0.001 mass %.

Among them, it is the most preferable to contain none (0 mass %) of the compound having a β-dicarbonyl structure. When the compound having a β-dicarbonyl structure is contained, the amount thereof is preferably no more than 0.0001 mass %.

The composition for whitening teeth may further contain a flavor ingredient other than isoamyl propionate, ethyl n-octanoate, and ethyl 3-methyl-3-phenylglycidate which does not have a β-dicarbonyl structure as another flavor ingredient. Examples of the other flavor ingredient include methyl anthranilate, allyl hexanoate, isoamyl isovalerate, limonene, ethyl hexanoate, ethyl butyrate, and ethyl maltol. Two or more of them may be employed in combination.

The composition for whitening teeth may contain a pH regulating ingredient. A basic substance is preferable as the pH regulating ingredient. Examples of a basic substance include sodium hydroxide, potassium hydroxide, magnesium hydroxide, and calcium hydroxide. Two or more of them may be employed in combination.

When the pH regulating ingredient is contained in the composition for whitening teeth, the amount thereof is preferably 0.1 mass % to 10 mass % on the basis of the total composition for whitening teeth although the pH regulating ingredient is used as suitably adjusted according to the material to be used. The amount of no less than 0.1 mass % promotes decalcification on surfaces of teeth, to improve the effect of whitening teeth. The amount of no more than 10 mass % makes it possible to suppress excess decalcification on surfaces of teeth.

The composition for whitening teeth may contain other chelating agent and coloring agent.

The composition for whitening teeth as described above can have a good flavor without deteriorating the function of the active ingredient for whitening.

For whitening discolored teeth using such a composition for whitening teeth, for example, the composition is employed by being directly applied to surfaces of teeth, or by attaching, to teeth, a tray that is especially for the composition for whitening teeth and in which the composition is put. The employment time of the composition for teeth is several minutes to several hours per one employment. The same operation may be repeated as necessary until a desired whitening effect is achieved.

EXAMPLES

<Making Composition for Whitening Teeth>
A composition for whitening teeth of each example was made as shown in Table 1 later.

Example 1

A vinyl polymer, and urea peroxide were added to a mixed solution of propylene glycol, glycerol, and water, to be stirred. When the solution was uniform, sodium hydroxide was added to the solution, to be neutralized. Isoamyl propionate, ethyl octanoate, and ethyl methyl phenylglycidate were further added to the obtained solution to be stirred, to make the composition for whitening teeth. The proportions of the amounts are as shown in Table 1.

Examples 2 to 9 and Comparative Examples 1 to 5

A composition for whitening teeth was made in the same way as in Example 1.
<Teeth Whitening Test and Evaluation>
An evulsed front tooth of cattle from which a tooth root portion was excised and thereafter the dental pulp was removed was used as a test piece for a whitening test. First, a color tone (values of L*, a* and b* in the CIE colorimetric system) of the surface of the test piece was measured. Values of L*, a* and b* were measured using CM-700d (manufactured by KONICA MINOLTA. INC.) at 100 in viewing angle, using illuminant D65, in a SCE mode.

Next, each of the prepared compositions for whitening teeth was applied to the test piece, thereafter kept at 37° C. in temperature at 100% in relative humidity for 2 hours, and thereafter washed with water.

After a series of these operations from application to washing was repeated fourteen times in total, the color tone (values of L*, a* and b* in the CIE colorimetric system) of the surface of the test piece was measured.

Then, the color difference ΔE*ab between the colors before and after the whitening was calculated from the following formula, to be a color change by whitening. In the following formula, ΔL* represents the difference between L* before and after the whitening, Δa* represents the difference between a* before and after the whitening, and Δb* represents the difference between b* before and after the whitening.

$$\Delta E^*ab=\{(\Delta L^*)^2+(\Delta a^*)^2+(\Delta b^*)^2\}^{0.5}$$

A larger color difference ΔE*ab represents that the whitening performance was higher. A case where ΔE*ab was more than 5 was evaluated as having a high whitening effect.
<Flavor Evaluation Test and Evaluation>
A flavor of each of the prepared compositions for whitening teeth was evaluated by ten professional panelists whether a good flavor was sensed as a composition to be employed intraorally.

In the evaluation on a scale of one to ten, 10 was very good, and 1 was very bad. A composition grated at no less than 6 in average in the results of the evaluation by the professional panelists was evaluated as having a good flavor.
<Results>
The results are shown together in Table 1. In Table 1, a blank represents 0 mass %.

TABLE 1

(Unit: mass %)

| | | | Ex. 1 | Ex. 2 | Ex. 3 | Ex. 4 | Ex. 5 | XEx. 6 | Ex. 7 | Ex. 8 | Ex. 9 |
|---|---|---|---|---|---|---|---|---|---|---|---|
| Ingredient | urea peroxide and/or hydrogen peroxide | urea peroxide | 10 | 10 | 10 | 10 | 10 | 10 | 10 | 10 | 10 |
| | thickener | vinyl polymer | 2 | 2 | 2 | 2 | 2 | 2 | 2 | 2 | 2 |
| | polyalcohol | propylene glycol | 35 | 35 | 35 | 35 | 35 | 35 | 35 | 35 | 35 |
| | | glycerol | 35 | 35 | 35 | 35 | 35 | 35 | 35 | 35 | 35 |
| | water | water | 16.7 | 16.5 | 16.996 | 16.65 | 16.9 | 15.48 | 16.43 | 16.975 | 16.499 |
| | pH regulating ingredient | sodium hydroxide | 1 | 1 | 1 | 1 | 1 | 1 | 1 | 1 | 1 |
| | specific flavor ingredient | isoamyl propionate | 0.15 | 0.2 | 0.001 | 0.1 | 0.01 | 0.5 | 0.07 | 0.002 | 0.2 |
| | | ethyl octanoate | 0.1 | 0.1 | 0.001 | 0.05 | 0.05 | 0.5 | 0.1 | 0.001 | 0.1 |
| | | ethyl methyl phenylglycidate | 0.65 | 0.2 | 0.002 | 0.1 | 0.01 | 0.5 | 0.15 | 0.002 | 0.2 |
| | other flavor ingredients | methyl anthranilate | | | | | | 0.01 | 0.05 | | |
| | | allyl hexanoate | | | | | | 0.01 | | 0.005 | |
| | | isoamyl isovalerate | | | | 0.1 | 0.01 | | | | |
| | | limonene | | | | | 0.01 | | | 0.005 | |
| | | ethyl hexanoate | | | | | 0.01 | | 0.2 | | |
| | | ethyl butyrate | | | | | | | | 0.005 | |
| | | ethyl maltol | | | | | | | | 0.005 | |
| | compound having a β-dicarbonyl structure | ethyl acetoacetate | | | | | | | | | 0.001 |
| Result | | whitening effect test (ΔE * ab) | 6.1 | 6.2 | 6.0 | 6.1 | 6.1 | 6.2 | 6.0 | 6.1 | 5.2 |
| | | flavor test | 7.1 | 7.5 | 7.4 | 8.5 | 8 | 6.8 | 7.4 | 7.1 | 7.4 |

| | | | Comp. Ex. 1 | Comp. Ex. 2 | Comp. Ex. 3 | Comp. Ex. 4 | Comp. Ex. 5 |
|---|---|---|---|---|---|---|---|
| Ingredient | urea peroxide and/or hydrogen peroxide | urea peroxide | 10 | 10 | 10 | 10 | 10 |
| | thickener | vinyl polymer | 2 | 2 | 2 | 2 | 2 |
| | polyalcohol | propylene glycol | 35 | 35 | 35 | 35 | 35 |
| | | glycerol | 35 | 35 | 35 | 35 | 35 |
| | water | water | 17 | 16.96 | 16.7 | 16.997 | 16.49 |
| | pH regulating ingredient | sodium hydroxide | 1 | 1 | 1 | 1 | 1 |
| | specific flavor ingredient | isoamyl propionate | | 0.02 | 0.2 | | 0.2 |
| | | ethyl octanoate | | | 0.1 | 0.001 | 0.1 |
| | | ethyl methyl phenylglycidate | | 0.02 | | 0.002 | 0.2 |
| | other flavor ingredients | methyl anthranilate | | | | | |
| | | allyl hexanoate | | | | | |
| | | isoamyl isovalerate | | | | | |
| | | limonene | | | | | |
| | | ethyl hexanoate | | | | | |
| | | ethyl butyrate | | | | | |
| | | ethyl maltol | | | | | |
| | compound having a β-dicarbonyl structure | ethyl acetoacetate | | | | | 0.01 |
| Result | | whitening effect test (ΔE * ab) | 6.2 | 6.1 | 6.0 | 6.2 | 2.3 |
| | | flavor test | 1.2 | 4.3 | 4.7 | 4.5 | 7.3 |

As is seen from Table 1, the composition for whitening teeth was able to have a good flavor without retarding a function of an active ingredient for whitening teeth but as keeping the whitening performance by containing isoamyl propionate, ethyl n-octanoate, and ethyl 3-methyl-3-phenyl-glycidate as a flavor ingredient, and either no more than 0.001 mass % or none of a compound having a β-dicarbonyl structure.

The invention claimed is:

1. A composition for whitening teeth, the composition comprising:

at least one of urea peroxide, and hydrogen peroxide;

isoamyl propionate in an amount of 0.01 mass % to 0.5 mass % on the basis of the composition;

ethyl n-octanoate in an amount of 0.001 mass % to 2 mass % on the basis of the composition;

ethyl 3-methyl-3-phenylglycidate in an amount of 0.001 mass % to 2 mass % on the basis of the composition; and a compound having a β-dicarbonyl structure in an amount of 0 mass % to 0.001 mass % on the basis of the composition.

* * * * *